United States Patent
Klipfel

(10) Patent No.: US 10,834,957 B2
(45) Date of Patent: Nov. 17, 2020

(54) METHOD AND APPARATUS FOR WINDING A SHEET OF HOMOGENIZED TOBACCO MATERIAL INTO A BOBBIN

(71) Applicant: PHILIP MORRIS PRODUCTS S.A., Neuchatel (CH)

(72) Inventor: Yorick Klipfel, St-Saphorin-sur-Morges (CH)

(73) Assignee: Philip Morris Products S.A., Neuchatel (CH)

(*) Notice: Subject to any disclaimer, the term of this patent is extended or adjusted under 35 U.S.C. 154(b) by 0 days.

(21) Appl. No.: 16/302,731

(22) PCT Filed: May 26, 2017

(86) PCT No.: PCT/EP2017/062747
§ 371 (c)(1),
(2) Date: Nov. 19, 2018

(87) PCT Pub. No.: WO2017/203030
PCT Pub. Date: Nov. 30, 2017

(65) Prior Publication Data
US 2019/0335802 A1    Nov. 7, 2019

(30) Foreign Application Priority Data
May 27, 2016  (EP) .................................. 16171641

(51) Int. Cl.
*A24B 3/14*   (2006.01)
*B65H 19/28*  (2006.01)
(Continued)

(52) U.S. Cl.
CPC ............... *A24B 3/14* (2013.01); *B65H 19/28* (2013.01); *G01N 33/0098* (2013.01); *A24C 5/20* (2013.01); *B65H 2801/54* (2013.01)

(58) Field of Classification Search
CPC .. B65H 19/28; B65H 2801/54; B65H 23/198; A24B 3/14; A24C 5/20; G01N 33/0098
See application file for complete search history.

(56) References Cited

U.S. PATENT DOCUMENTS 3,398,754 A * 8/1968 Tughan .................. A24B 15/12
                                                    131/374
3,473,535 A * 10/1969 Stahly .................... A24B 15/10
                                                    131/336
(Continued)

FOREIGN PATENT DOCUMENTS

WO   WO 2015/193031   12/2015

OTHER PUBLICATIONS

PCT Search Report and Written Opinion for PCT/EP2017/062747 dated Oct. 19, 2017 (11 pages).

*Primary Examiner* — William A. Rivera
(74) *Attorney, Agent, or Firm* — Mueting Raasch Group

(57) ABSTRACT

The invention relates to a method for winding a sheet (13) of homogenized tobacco material into a bobbin (12), the method comprising: providing a sheet of homogenized tobacco material having a free end (11); connecting the free end to a center core; rotating the center core so as to wind the sheet of homogenized tobacco material around it forming the bobbin; and applying a force per unit length to the sheet of homogenized tobacco material during winding to pull the same having a magnitude comprised between about 42 N/m and about 93 N/m.

9 Claims, 1 Drawing Sheet

(51) Int. Cl.
*G01N 33/00* (2006.01)
*A24C 5/20* (2006.01)

(56) References Cited

U.S. PATENT DOCUMENTS

| | | | |
|---|---|---|---|
| 3,738,587 A | 6/1973 | Cristiani | |
| 2003/0226928 A1 | 12/2003 | McNeil | |
| 2005/0056294 A1* | 3/2005 | Wanna | A24B 3/14 |
| | | | 131/372 |
| 2015/0314982 A1* | 11/2015 | Barea | B65H 59/388 |
| | | | 242/419.1 |
| 2017/0273346 A1* | 9/2017 | Klipfel | A24B 3/14 |
| 2017/0273348 A1* | 9/2017 | Klipfel | A24B 3/08 |
| 2017/0340001 A1* | 11/2017 | Soo | A24B 15/12 |
| 2017/0340002 A1* | 11/2017 | Soo | A24B 15/12 |
| 2018/0332884 A1* | 11/2018 | Rosado | A24B 3/14 |
| 2018/0368465 A1* | 12/2018 | Rosado | A24B 3/14 |

* cited by examiner

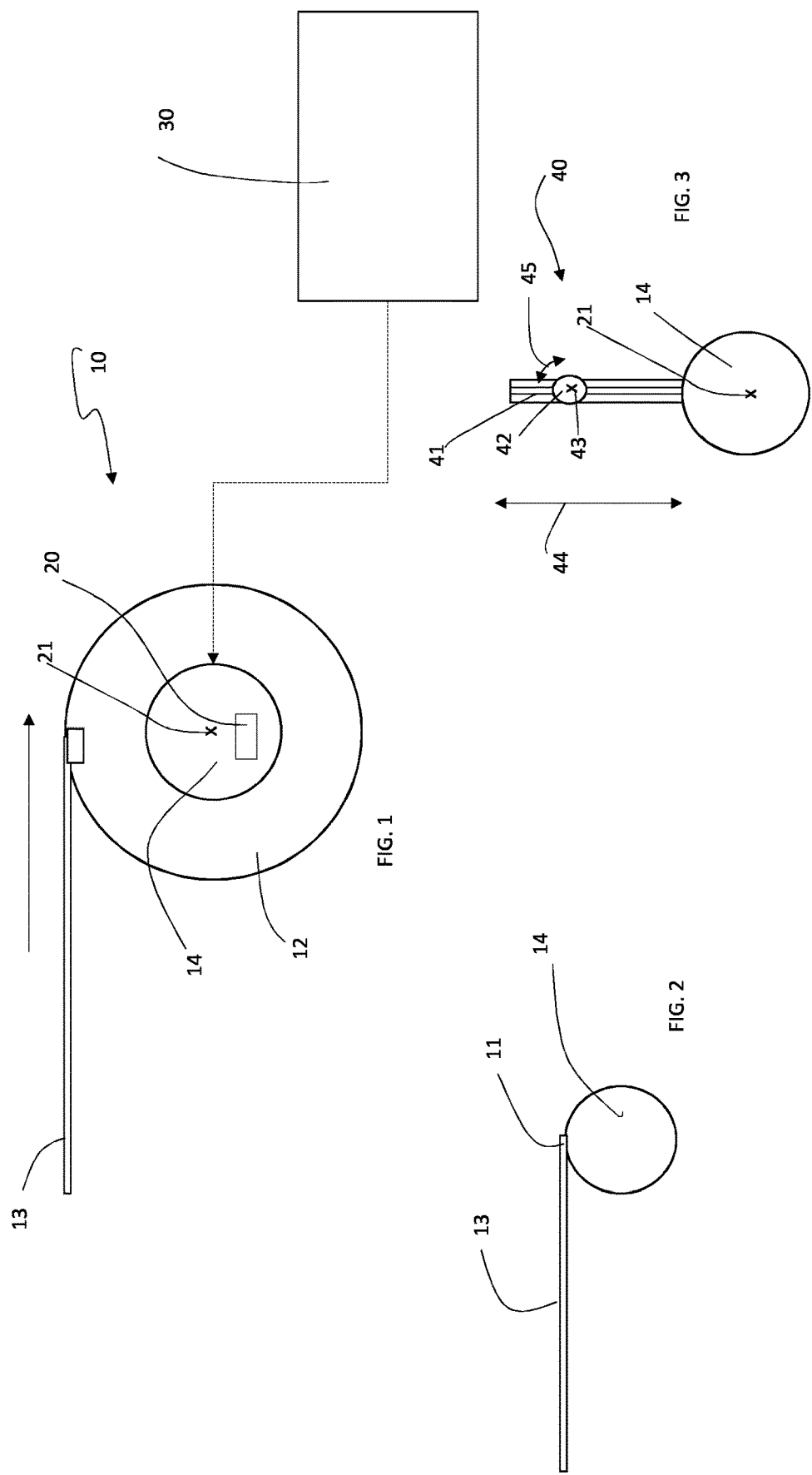

METHOD AND APPARATUS FOR WINDING A SHEET OF HOMOGENIZED TOBACCO MATERIAL INTO A BOBBIN

This application is a U.S. National Stage Application of International Application No. PCT/EP2017/062747 filed May 26, 2017, which was published in English on Nov. 30, 2017, as International Publication No. WO 2017/203030 A1. International Application No. PCT/EP2017/062747 claims priority to European Application No. 16171641.0 filed May 27, 2016.

The present invention is related to a method and an apparatus to wind a sheet of homogenized tobacco material into a bobbin.

Unwinding bobbins of material can be a difficult task, when the material which is coiled to form a bobbin is at the same time both sticky, so a rather high force need to be applied in order to unwind it, and fragile, so that it can be easily torn apart. Such a material is for example homogenized tobacco sheet, which can be obtained for example casting a sheet of homogenized tobacco material. The homogenized tobacco sheet, when coiled in bobbins, is difficult to unwind due to its consistency, sensitivity to heat and low tensile strength, all preventing for instance to simply increase the force applied to the sheet to unwind the bobbin. In current manufacturing process of homogenized tobacco material, unwinding speed has to be lowered sometimes down to about 100 meters per minute in order to prevent as much as possible to tear the homogenized tobacco sheet, which in turn automatically decreases the production speed and hourly production.

In addition to the low tensile strength of the material, some bobbins of homogenized tobacco sheet have quite variable shapes from one to another, so this shape inhomogeneity has to be taken into account in an apparatus and a method to unwind bobbins of homogenized tobacco sheet.

There is therefore a need of a method and an apparatus to wind a sheet of homogenized tobacco material that allow to reach higher unwinding speed without damaging the homogenized tobacco sheet itself.

These method and apparatus should be capable to wind a bobbin of homogenized tobacco material so that, when the bobbin is to be unwound, the unwinding speed is increased compared to the previous methods and apparatuses so that the rest of the production line can increase the overall production rate.

In an aspect, the invention relates to a method for winding a sheet of homogenized tobacco material into a bobbin, the method comprising: providing a sheet of homogenized tobacco material having a free end; connecting the free end to a center core; rotating the center core so as to wind the sheet of homogenized tobacco material around it forming the bobbin; and applying a force per unit length to the sheet of homogenized tobacco material during winding to pull the same having a magnitude comprised between about 42 N/m and about 93 N/m.

Winding a bobbin of homogenized tobacco material with a pulling force whose magnitude is comprised about 42 N/m and about 93 N/m allows obtaining bobbins that are more easily unwound than if the homogenized tobacco sheet is pulled while winding with a force having a magnitude outside this range. The method of the invention may prevent or lower the probability to create sticky homogenized tobacco material bobbins, that is, bobbins in which the layers of the wound homogenized tobacco material stick one to the other, preventing or hindering the unwinding. This in turn may help to increase the unwinding speed of homogenized tobacco material bobbins. Further, the pulling force may be adjustable to different magnitudes depending on different compositions of the homogenized tobacco material or other characteristics of the outer ambient surrounding it.

As used herein, the term "sheet" denotes a laminar element having a length and length substantially greater than the thickness thereof. The width of a sheet is preferably greater than 10 millimeters, more preferably greater than 20 millimeters or 30 millimeters. Even more preferably, the width of the sheet is comprised between about 100 millimeters and 300 millimeters.

In a preferred embodiment, the sheet is a sheet of homogenized tobacco material.

The most commonly used forms of homogenized tobacco material is reconstituted tobacco sheet and cast leaf. The process to form homogenized tobacco material sheets commonly comprises a step in which tobacco dust and a binder, are mixed to form a slurry. The slurry is then used to create a tobacco web. For example by casting a viscous slurry onto a moving metal belt to produce so called cast leaf. Alternatively, a slurry with low viscosity and high water content can be used to create reconstituted tobacco in a process that resembles paper-making.

The sheet material of tobacco can be referred to as a reconstituted sheet material and formed using particulate tobacco (for example, reconstituted tobacco) or a tobacco particulate blend, a humectant and an aqueous solvent to form the tobacco composition. This tobacco composition is then casted, extruded, rolled or pressed to form a sheet material from the tobacco composition. The sheet of tobacco can be formed utilizing a wet process, where tobacco fines are used to make a paper-like material; or a cast leaf process, where tobacco fines are mixed together with a binder material and cast onto a moving belt to form a sheet.

The sheet of homogenized tobacco material is then rolled in bobbins which needs to be unwound in order to be further processed, to be part for example of an aerosol-forming article, that is to be included in the aerosol-forming substrate of the aerosol-forming article. In a "heat-not-burn" aerosol-generating article, an aerosol-forming substrate is heated to a relatively low temperature, in order to form an aerosol but prevent combustion of the tobacco material. Further, the tobacco present in the homogenized tobacco sheet is typically the only tobacco, or includes the majority of the tobacco, present in the homogenized tobacco material of such a "heat-not-burn" aerosol-generating article. This means that the aerosol composition that is generated by such a "heat-not-burn" aerosol-generating article is substantially only based on the homogenized tobacco material.

As used herein, the term "aerosol forming material" denotes a material that is capable of releasing volatile compounds upon heating to generate an aerosol. Tobacco may be classed as an aerosol forming material, particularly a sheet of homogenized tobacco comprising an aerosol former. An aerosol forming substrate may comprise or consist of an aerosol forming material.

The homogenized tobacco sheet generally includes, in addition to the tobacco, a binder and an aerosol-former. This composition leads to a sheet which is "sticky", that is, it glues to adjacent objects, and at the same time it is rather fragile having a relatively low tensile strength.

The bobbin shape can be any. It can have a substantially cylindrical shape, however an oval or anyhow deformed shape, such as a bobbin with bulges deforming a underlying cylindrical shape, does not hinder the application of the teaching of the invention.

In order to properly unwind the bobbin, keeping in mind its stickiness and fragility and thus minimizing breakage but at the same time keeping a relatively high unwinding speed, it is thus preferably formed a bobbin according to the method of the invention. According to the method of the invention, the homogenized tobacco material that is wound sticks as less as possible among the different wound layers laying one on top of the others.

A free end of the tobacco sheet, for example the whole width of the free end, is connected to a center core of a bobbin. The center core can also have any shape, for example it can be cylindrical, but it can also have an elliptic cross section. In order to form the bobbin, the center core to which the free end of the sheet is connected starts rotating, so that the sheet can be wound around the center core. While rotating, therefore, a layer of sheet is continuously wound on top of an already wound layer of sheet and thus a bobbin is formed, piling up several layers which are wound one on top of the other. In the following, a "layer" of the sheet wound in the bobbin has therefore the meaning of a portion of the homogenized tobacco material sheet that forms a substantially closed loop wound around the center core. Each layer is generally, with the exception of the first and the last layer, in contact with a lower layer and an upper layer. The geometrical shape formed by the layer could be, for example in a section perpendicular to the winding axis of the center core of the bobbin, a circle or an ellipse.

In order to form the bobbin, the sheet needs to be pulled so that it can be wound around the center core. Therefore, a "pulling force" pulls the sheet while the center core rotates around an axis. Preferably, the pulling force is measured at the boundary between the already wound layer and the free portion of the homogenized tobacco material. That is, the pulling force is measured along a line of junction between the already wound layer in the bobbin and the remaining of the homogenized tobacco sheet.

However, exerting a pulling force onto the homogenized tobacco sheet to wind it up into a bobbin creates at least two kinds of effect on the sheet itself.

The first effect is that the winding up action by itself exerts a force pressing the external layers toward the internal layers of the already wound homogenized tobacco material.

The second effect takes place due to the fact that the homogenized tobacco sheet is elastic, at least partly, due to its composition. The pulling force stretches the sheet. A portion of elastic sheet that has been stretched, when being afterwards a layer on the bobbin, tends to decrease the stretching tension by shortening itself. When the layer is part of a bobbin, this can only be achieved by the aforementioned layer by decreasing the perimeter of the closed loop formed by the layer itself, for example in case of a circular layer, by decreasing the diameter of the "circle" made by the layer. Due to the shortening of the perimeter of the closed loop formed by the layer, a compression force builds up, that is, the layer which gets shorter presses—with a force directed toward the axis of the center core of the bobbin—the layers below it.

The higher the magnitude of the pulling force, the higher the pressing force that a layer of homogenized tobacco material exerts on the layers underneath, so that the homogenized tobacco material layers are pressed one on another, generating conditions for "sticky" bobbins, in which the layers are substantially glued one to the others.

By pulling the homogenized tobacco sheet with a force having a magnitude within the indicated specific range, the homogenized tobacco sheet elastic fabric is not too much elongated along the bobbin perimeter during the winding up of the bobbin. In this way, the external layers of the bobbin may not compress too much the internal layers, suppressing or decreasing one cause of the stickiness effect.

Using the indicated range of magnitude for the pulling force instead of a higher pulling force may decrease the theoretical maximal productivity of the tobacco bobbins manufacturing. However, by decreasing the time needed to unwind the bobbin as well as decreasing the quantity of waste, according to the invention, the productivity of the overall process may be increased. Simplifying the unwinding speeds up the subsequent processes, compensating for a lower winding step.

Further, the pulling force having a magnitude within the claimed range is preferably below the ultimate tensile strength of the homogenized tobacco material. Therefore, pulling the homogenized tobacco sheet with a force having a magnitude within the claimed range avoids tearing the homogenized tobacco sheet.

Preferably, the force per unit length has a direction tangent to an outer surface of said bobbin. Preferably, the bobbin is wound in such a way that a portion of the homogenized tobacco sheet that is wound is kept tangent to the external surface of the bobbin, that is, the sheet still to be wound is kept tangent to the most external layer of the bobbin. The force which pulls the bobbin is thus directed also tangent to the external layer of the bobbin. This force, as mentioned, is measured at the junction between the most external layer of the bobbin that has been already wound and the free portion of the sheet that is not in contact with the rest of the bobbin yet. The pulling force is substantially a uniaxial force, preferably substantially perpendicular to the rotation axis of the center core.

The force per unit length is substantially a force per unit "width" so that in a width of the sheet of about 12-14 centimeters a force of about 6-9 Newton is applied.

Preferably, the method of the invention comprises one or more of the following: determining the composition of the sheet of homogenizing tobacco material; determining the grammage of the sheet of homogenizing tobacco material; determining one or more parameters of an ambient where the sheet of homogenizing tobacco material is located; determining the humidity of the sheet of homogenizing tobacco material; and it also comprises varying the value of the force per unit width used to pull the sheet of homogenized tobacco material during winding depending on the value of one or more between the composition, the grammage, one or more parameters of the ambient, or the humidity of said sheet of homogenizing tobacco material. Being the pulling force generated by the rotation of the center core, it is relatively easy to change the same, by changing the way in which the rotation of the center core is performed. Depending on one or more of the characteristics of the homogenized tobacco sheet, it is relatively easy to adapt the winding to the specificity of the homogenized tobacco sheet itself, performing an optimal winding process. Therefore, depending on for example the humidity, the grammage or the composition of the homogenized tobacco sheet, the pulling force magnitude can be properly set. Further, the winding may be adapted to the ambient conditions, determining one or more of them, such as the air humidity or temperature, and setting the optimal pulling force in dependence of them.

Preferably, the method of the invention comprises: selecting a sub-range of forces magnitudes within the range of magnitudes of forces per unit length of between about 42 N/m and about 93 N/m; and during winding of the bobbin, keeping the magnitude of force per unit length used to pull said sheet of homogenized tobacco material during winding within said sub-range. During the winding of the bobbin, preferably the pulling force magnitude per unit length is kept within a sub range of the claimed range of magnitudes, that is, it is kept within a subrange of between about 42 N/m and about 93 N/m. This allows to better control the winding process, instead of keeping always the same set magnitude, but allowing small variations of the same.

Preferably, the method includes measuring a diameter of the bobbin while winding. More preferably, the method includes: measuring an electrical resistance between a surface of the bobbin and the center core; detecting the electrical resistance variations during winding so as to calculate the diameter of the bobbin. The pulling force magnitude to be applied to the homogenized tobacco sheet, in order to be kept preferably either substantially constant or within a sub-range of the claimed range of magnitudes, may also depend on the diameter of the bobbin. Preferably, therefore, the diameter of the bobbin, which increases during winding, is continuously checked or it is monitored. The diameter of the bobbin may also determine when the winding process is to be terminated, so that not too large bobbins are created. The diameter of the bobbin can be determined and controlled in a relatively easy manner detecting the electrical resistance between the center core and the outer layer of the bobbin, which changes depending on the diameter of the bobbin itself.

Preferably, the method of the invention includes generating said force per unit length by rotating the center core by means of an electric motor. More preferably, the method includes changing the power absorbed by the motor as a function of a diameter of the bobbin during winding of the bobbin. Even more preferably, the method comprises increasing the power absorbed by the motor while increasing the diameter of the bobbin. An electrical motor may be used to automatically rotate the center core. According to the physical law $$P = F\left(\frac{D}{2}\right)\omega \qquad \text{Eq. (1)}$$

where P: mechanical power of the motor;
F: force exerted at the peripheral of the bobbin, that is, at its outer layer;
D: diameter of the bobbin; and
ω: angular velocity, considering the angular velocity substantially constant, when the diameter D of the bobbin increases due to the winding of the bobbin, the force F exerted on the homogenized tobacco sheet decreases if the power, that is the electrical power absorbed, is not increased accordingly. Thus, in order to keep the force magnitude substantially constant or within a specified sub-range, it is preferred to vary the power absorbed by the motor while winding the bobbin.

Preferably, the diameter of the bobbin is comprised between about 200 millimeters and about 800 millimeters.

Preferably, the method of the invention comprises: keeping an angular velocity of said center core substantially constant during winding of the bobbin. A regular motion of the bobbin is preferably achieved without accelerations or decelerations which may hinder the correct positioning of the various layers of the homogenized tobacco sheet one on top of the other.

According to a further aspect, the invention relates to a winding apparatus for winding a sheet of homogenized tobacco material into a bobbin, the apparatus comprising: a rotatable center core around which the sheet of homogenized tobacco is wound; a motor to rotate the center core in order to wind the sheet of homogenized tobacco material around the center core; and a power control apt to control the power absorbed by the motor while rotating said center core so that it generates a pulling force per unit length to pull said sheet of homogenized tobacco material having a magnitude comprised between about 42 N/m and about 93 N/m. Advantages of such an apparatus have been already discussed with reference to the first aspect of the invention and are not herewith repeated.

Preferably, the winding apparatus includes a sensor to measure the diameter of the bobbin. More preferably, said sensor is a resistive sensor. Even more preferably, said sensor includes a roller apt to rotate on an external surface of said bobbin and a rail in which the roller is slidable, said rail extending perpendicularly to an axis of the center core. A sensor to measure the bobbin diameter could include a roller rolling on the outside surface of the bobbin. Further, the roller can move along a rail perpendicular to the bobbin axis and extending from the location of the bobbin axis, that is, from the center core, radially to the outside. While the bobbin is formed, winding the sheet of homogenized tobacco material, the distance between the roller and the center core increases, and the roller shifts along the rail. The distance between the beginning of the rail at the center core and the position of the roller thus increases while the bobbin increases its diameter. The portion of the rail between the roller and the bobbin axis could be used as an electrical resistance: determining the value of the electrical resistance also determines the diameter of the bobbin.

Preferably, said sensor is a contactless distance sensor apt to emit electromagnetic radiation towards a surface of said bobbin and to detect the reflected electromagnetic radiation from the surface.

Preferably, the winding apparatus includes a control apt to change the magnitude of the pulling forced per unit length within the range between about 42 N/m and about 93 N/m. The control can be automatic or it can be operated by an operator. The pulling force may be set at the beginning of the winding of a bobbin and may remain substantially constant along the whole winding of a bobbin, or it may change during winding. In the latter case, it may be changed due to varied ambient conditions. Further, the pulling force magnitude may be set according to the type of homogenized tobacco sheet.

Further advantages of the invention will become apparent from the detailed description thereof with no-limiting reference to the appended drawings:

FIG. 1 is a schematic lateral view of a winding apparatus according to the invention for winding a bobbin;

FIG. 2 is a further schematic view of the winding apparatus of FIG. 1, at the beginning of the winding process; and FIG. 3 is a lateral view of the winding apparatus of FIG. 1 or 2 without the homogenized tobacco sheet.

With reference to the figures, a winding apparatus for winding a bobbin according to the present invention is represented and indicated with reference number 10.

The apparatus 10 is adapted to wind a bobbin 12. For instance, the bobbin 12 can be a homogenized tobacco material bobbin. The bobbin 12 shown in the figures has a round, for example cylindrical, shape. However, the invention works fine with bobbins even when the bobbins do not have round shape.

The apparatus 10 comprises a bobbin holder 14 or center core where the bobbin 12 is placed.

The bobbin 12 is formed by a homogenized tobacco sheet 13. The apparatus 10 is adapted to wind the homogenized tobacco sheet 13 of the bobbin 12, as shown in FIG. 1.

The apparatus 10 also comprises a motor 20 and a control unit 30, both schematically depicted in FIG. 1 as rectangles. The motor 20 is coupled to bobbin holder and is adapted to rotate the same along an axis 21 of the bobbin holder. For example, in case the bobbin holder 14 is a cylinder, axis 21 is the axis of the cylinder.

The control unit 30 is connected to motor 20 and is adapted to control, among others, the power absorbed by the motor, the speed of the motor, and other variables.

Further, apparatus 10, as shown in FIG. 3, includes a diameter sensor 40 adapted to measure the diameter of the bobbin 12 during winding. The diameter sensor 40 includes a rail 41 extending from the bobbin holder 14 along a radius of a cross section of the same, and preferably from its axis 21, for a given length, preferably longer than the maximum diameter reachable by a bobbin. In the rail 41, a roller 42 can slide, so as to translate along the rail. Further, roller 42 can also rotate along an axis 43, preferably parallel to the axis 21 of the bobbin holder 14. The roller 42 can shift along rail up and down along the arrow 44 depicted in FIG. 3 and rotate along its axis as depicted by arrow 45 also shown in FIG. 3.

The winding of the homogenized tobacco sheet 13 to form bobbin 12 takes place as follows. First, a free end 11 of the homogenized tobacco sheet 13 is connected to the bobbin holder 14. The connection takes place in such a way that the free end 11 of the sheet 13 extends tangent to the bobbin holder 14. The bobbin holder 14 is then rotated by means of motor 20, while keeping the sheet 13 tangent to the bobbin that forms winding one layer on top of the other of the sheet 13.

The control unit 30 controls motor 20 so that the angular velocity of bobbin holder 14 remains substantially constant. Further, the control unit 30 controls the power absorbed by motor 20 so that the pulling force 50 (depicted as an arrow in FIG. 1) per unit length with which the sheet is pulled at the junction between a free portion of the sheet and the bobbin where the layers of the sheet are wound is comprised between about 42 N/m and about 93 N/m.

In order to determine the power to be absorbed by the motor, preferably the diameter of the bobbin is checked by means of sensor 40. The distance between roller 42 which rotates on the free surface of the bobbin, that is, on the last wound layer of the sheet 13, and the axis 21 varies with the increasing diameter size of the bobbin 12. An electrical resistance between the two points in the rail 42 where the roller 42 is and the center of the bobbin holder, that is, the position of axis 21, is determined during the winding, obtaining a value of the bobbin diameter.

From the equation (1), the power is determined, power controller by control unit 30. Preferably, the control unit 30 controls the power absorbed by motor 20 so that the pulling force magnitude remains substantially constant during winding or that the pulling force magnitude remains within a sub-range of the range comprised between about 42 N/m and about 93 N/m.

The optimal pulling force 50 is determined on the basis of characteristics of the sheet 13, for example its composition, grammage and humidity, and/or on the basis of parameters of the ambient where the sheet 13 is wound, for example on the basis of the humidity of air, its temperature and others.

During winding, the pulling force magnitude can be changed, for example if the ambient condition changes. The control unit 30 consequently varies the controlling parameters of the motor 20.

The invention claimed is:

1. Method for winding a sheet of homogenized tobacco material into a bobbin, the method comprising:
    providing a sheet of homogenized tobacco material having a free end, including:
        forming a tobacco composition using particulate tobacco or a tobacco particulate blend, a humectant and an aqueous solvent to form the tobacco composition; and
        casting, extruding, rolling, or pressing the tobacco composition to form the sheet of homogenized material from the tobacco composition;
    connecting the free end to a center core;
    rotating the center core so as to wind the sheet of homogenized tobacco material around the center core to form the bobbin;
    applying a force per unit length to the sheet of homogenized tobacco material during winding to pull the same having a magnitude comprised between about 42 N/m and about 93 N/m;
    determining one or more parameters of an ambient where the sheet of homogenizing tobacco material is located;
    selecting a sub-range of force's magnitudes within the range of magnitudes of forces per unit length of between about 42 N/m and about 93 N/m; and
    during winding of the bobbin, varying the value of the force per unit length used to pull said sheet of homogenized tobacco material within said sub-range depending on the value of the one or more parameters of the ambient.

2. The method according to claim 1, wherein the force per unit length has a direction tangent to an outer surface of said bobbin.

3. The method according to claim 1, comprising one or more of the following:
    determining the composition of the sheet of homogenizing tobacco material;
    determining the grammage of the sheet of homogenizing tobacco material;
    determining the humidity of the sheet of homogenizing tobacco material;
and it also comprises:
    varying the value of the force per unit length used to pull the sheet of homogenized tobacco material during winding depending on the value of one or more between the composition, the grammage, or the humidity of said sheet of homogenizing tobacco material.

4. The method according to claim 1, comprising:
measuring a diameter of the bobbin while winding.

5. The method according to claim 4, including:
measuring an electrical resistance between a surface of the bobbin and the center core; and
detecting electrical resistance variations during winding so as to calculate the diameter of the bobbin.

6. The method according to claim 1, comprising:
generating said force per unit length by rotating the center core by means of an electric motor.

7. The method according to claim 6, comprising:
changing the power absorbed by the motor as a function of a diameter of the bobbin during winding of the bobbin.

8. The method according to claim 7, comprising:
increasing the power absorbed by the motor while increasing the diameter of the bobbin.

9. The method according to claim 1, comprising:
keeping an angular velocity of said center core substantially constant during winding of the bobbin.

\* \* \* \* \*